(12) United States Patent
Montanari et al.

(10) Patent No.: US 11,970,798 B2
(45) Date of Patent: Apr. 30, 2024

(54) GRIPPING FABRIC COATED WITH A BIORESORBABLE IMPENETRABLE LAYER

(71) Applicant: SOFRADIM PRODUCTION, Trevoux (FR)

(72) Inventors: Suzelei Montanari, Trevoux (FR); Yves Bayon, Lyons (FR); Xavier Bourges, Mogneneins (FR); Delphine Petit, Montanay (FR)

(73) Assignee: SOFRADIM PRODUCTION, Trevoux (FR)

(*) Notice: Subject to any disclaimer, the term of this patent is extended or adjusted under 35 U.S.C. 154(b) by 447 days.

(21) Appl. No.: 17/117,083

(22) Filed: Dec. 9, 2020

(65) Prior Publication Data

US 2021/0189616 A1  Jun. 24, 2021

Related U.S. Application Data

(62) Division of application No. 13/393,994, filed as application No. PCT/EP2010/063062 on Sep. 6, 2010, now Pat. No. 10,865,505.

(30) Foreign Application Priority Data

Sep. 4, 2009 (FR) ..................... 0956039

(51) Int. Cl.
*D04B 21/12* (2006.01)
*A61F 2/00* (2006.01)
(Continued)

(52) U.S. Cl.
CPC ............ *D04B 21/12* (2013.01); *A61F 2/0063* (2013.01); *A61L 27/34* (2013.01); *A61L 27/50* (2013.01);
(Continued)

(58) Field of Classification Search
CPC ...................................................... D04B 21/12
See application file for complete search history.

(56) References Cited

U.S. PATENT DOCUMENTS 1,187,158 A   6/1916 Mcginley
3,118,294 A   1/1964 Van Laethem
(Continued)

FOREIGN PATENT DOCUMENTS

CA   1317836 C    5/1993
DE   19544162 C1  4/1997
(Continued)

OTHER PUBLICATIONS

Amid, P., "Lichtenstein tension-free hernioplasty: Its inception, evolution, and principles," Hernia, 2004; pp. 1-7, 8, published online Sep. 2003.
(Continued)

*Primary Examiner* — Dah-Wei D. Yuan
*Assistant Examiner* — Andrew J Bowman
(74) *Attorney, Agent, or Firm* — Weber Rosselli & Cannon LLP

(57) ABSTRACT

The present invention relates to a prosthetic fabric (5) comprising an arrangement (2) of yarns that define at least first and second opposite faces (2a, 2b) for said fabric, said fabric comprising on at least said first face, one or more barbs (3) that protrude outwards relative to said first face, said fabric being covered, at least partly, on said second face with a microporous layer made of a bioresorbable material, said barbs being covered with a coating made of a water-soluble material. The invention also relates to a process for obtaining such a fabric and to prostheses obtained from such a fabric.

19 Claims, 2 Drawing Sheets

(51) Int. Cl.
*A61L 27/34* (2006.01)
*A61L 27/50* (2006.01)
*A61L 27/54* (2006.01)
*A61L 27/56* (2006.01)
*A61F 2/30* (2006.01)

(52) U.S. Cl.
CPC .............. *A61L 27/54* (2013.01); *A61L 27/56* (2013.01); *A61F 2/0077* (2013.01); *A61F 2002/30322* (2013.01); *A61F 2220/0016* (2013.01); *A61F 2250/0026* (2013.01); *A61F 2250/0031* (2013.01); *A61L 2300/61* (2013.01); *D10B 2403/0112* (2013.01); *D10B 2501/0632* (2013.01); *D10B 2509/08* (2013.01)

(56) References Cited

U.S. PATENT DOCUMENTS

| | | |
|---|---|---|
| 3,124,136 A | 3/1964 | Usher |
| 3,272,204 A | 9/1966 | Artandi et al. |
| 3,276,448 A | 10/1966 | Kronenthal |
| 3,320,649 A | 5/1967 | Naimer |
| 3,364,200 A | 1/1968 | Ashton et al. |
| 3,511,904 A | 5/1970 | Griset |
| 3,570,482 A | 3/1971 | Shigeru et al. |
| 4,006,747 A | 2/1977 | Kronenthal et al. |
| 4,060,081 A | 11/1977 | Yannas et al. |
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,374,669 A | 2/1983 | MacGregor |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,376,375 A | 12/1994 | Rhee et al. |
| 5,376,376 A | 12/1994 | Li |
| 5,383,897 A | 1/1995 | Wholey |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |

(56) References Cited

U.S. PATENT DOCUMENTS

| | | |
|---|---|---|
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,964,782 A | 10/1999 | Lafontaine et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,036 B1 | 3/2001 | Tripp et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Robert |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Mueller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Bryan et al. |
| 6,723,335 B1 | 4/2004 | Moehlenbruck et al. |
| 6,730,299 B1 | 5/2004 | Tayot et al. |
| 6,743,435 B2 | 6/2004 | Devore et al. |
| 6,755,868 B2 | 6/2004 | Rousseau |
| 6,773,723 B1 | 8/2004 | Spiro et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,670,380 B2 | 3/2010 | Cauthen, III et al. |
| 2001/0008930 A1 | 7/2001 | Tayot et al. |
| 2002/0052612 A1 | 5/2002 | Schmitt et al. |
| 2002/0077661 A1 | 6/2002 | Saadat |
| 2002/0087184 A1 | 7/2002 | Eder et al. |
| 2002/0095218 A1 | 7/2002 | Carr et al. |
| 2002/0116070 A1 | 8/2002 | Amara et al. |
| 2002/0133232 A1 | 9/2002 | Ricci et al. |
| 2003/0013989 A1 | 1/2003 | Obermiller et al. |
| 2003/0023316 A1 | 1/2003 | Brown et al. |
| 2003/0040809 A1 | 2/2003 | Goldmann et al. |
| 2003/0086975 A1 | 5/2003 | Ringeisen |

(56) References Cited

U.S. PATENT DOCUMENTS

| | | |
|---|---|---|
| 2003/0100954 A1 | 5/2003 | Schuldt-Hempe et al. |
| 2003/0100955 A1 | 5/2003 | Greenawalt et al. |
| 2003/0114937 A1 | 6/2003 | Leatherbury et al. |
| 2003/0133967 A1 | 7/2003 | Ruszczak et al. |
| 2003/0212460 A1 | 11/2003 | Darois et al. |
| 2003/0225355 A1 | 12/2003 | Butler |
| 2003/0232746 A1 | 12/2003 | Lamberti et al. |
| 2004/0034373 A1 | 2/2004 | Schuldt-Hempe et al. |
| 2004/0054406 A1 | 3/2004 | Dubson et al. |
| 2004/0059356 A1 | 3/2004 | Gingras |
| 2004/0101546 A1 | 5/2004 | Gorman et al. |
| 2004/0132365 A1 | 7/2004 | Therin et al. |
| 2004/0138762 A1 | 7/2004 | Therin et al. |
| 2004/0172048 A1 | 9/2004 | Browning |
| 2004/0215219 A1 | 10/2004 | Eldridge et al. |
| 2005/0002893 A1 | 1/2005 | Goldmann |
| 2005/0010078 A1 | 1/2005 | Jamiolkowski et al. |
| 2005/0010306 A1 | 1/2005 | Priewe et al. |
| 2005/0021058 A1 | 1/2005 | Negro |
| 2005/0043786 A1 | 2/2005 | Chu et al. |
| 2005/0058684 A1 | 3/2005 | Shanley et al. |
| 2005/0079201 A1 | 4/2005 | Rathenow et al. |
| 2005/0085924 A1 | 4/2005 | Darois et al. |
| 2005/0113849 A1 | 5/2005 | Popadiuk et al. |
| 2005/0113938 A1 | 5/2005 | Jamiolkowski et al. |
| 2005/0125077 A1 | 6/2005 | Harmon et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0149173 A1 | 7/2005 | Hunter et al. |
| 2005/0175659 A1 | 8/2005 | Macomber et al. |
| 2005/0228408 A1 | 10/2005 | Fricke et al. |
| 2005/0232979 A1 | 10/2005 | Shoshan |
| 2005/0244455 A1 | 11/2005 | Greenawalt |
| 2005/0267521 A1 | 12/2005 | Forsberg |
| 2005/0283256 A1 | 12/2005 | Sommerich et al. |
| 2005/0288691 A1 | 12/2005 | Leiboff |
| 2006/0094318 A1 | 5/2006 | Matsuda et al. |
| 2006/0135921 A1 | 6/2006 | Wiercinski et al. |
| 2006/0147501 A1 | 7/2006 | Hillas et al. |
| 2006/0167540 A1 | 7/2006 | Masters et al. |
| 2006/0167561 A1 | 7/2006 | Odar et al. |
| 2006/0216320 A1 | 9/2006 | Kitazono et al. |
| 2006/0252981 A1 | 11/2006 | Matsuda et al. |
| 2007/0031474 A1 | 2/2007 | Tayot et al. |
| 2007/0100432 A1 | 5/2007 | Case et al. |
| 2007/0156238 A1 | 7/2007 | Liao et al. |
| 2007/0161109 A1 | 7/2007 | Archibald et al. |
| 2007/0207186 A1 | 9/2007 | Scanlon et al. |
| 2007/0239265 A1 | 10/2007 | Birdsall |
| 2007/0244569 A1 | 10/2007 | Weber et al. |
| 2007/0280990 A1 | 12/2007 | Stopek |
| 2007/0297987 A1 | 12/2007 | Stad et al. |
| 2007/0299538 A1 | 12/2007 | Roeber |
| 2008/0086216 A1 | 4/2008 | Wilson et al. |
| 2008/0132922 A1 | 6/2008 | Buevich et al. |
| 2009/0004239 A1 | 1/2009 | Ladet et al. |
| 2009/0024151 A1 | 1/2009 | Shalaby et al. |
| 2009/0036997 A1 | 2/2009 | Bayon et al. |
| 2009/0192532 A1* | 7/2009 | Spinnler ............... D04B 21/12 606/153 |
| 2010/0016872 A1 | 1/2010 | Bayon et al. |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 0544485 A1 | 6/1993 |
| EP | 0552576 A1 | 7/1993 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0827724 A2 | 3/1998 |
| EP | 0836838 A1 | 4/1998 |
| EP | 0895762 A2 | 2/1999 |
| EP | 0898944 A2 | 3/1999 |
| EP | 1017415 A1 | 7/2000 |
| EP | 1052319 A1 | 11/2000 |
| EP | 1055757 A1 | 11/2000 |
| EP | 1216717 A1 | 6/2002 |
| EP | 1216718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2715405 A1 | 7/1995 |
| FR | 2724563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 B1 | 12/2005 |
| FR | 2863277 B1 | 6/2006 |
| FR | 2884706 B1 | 4/2008 |
| FR | 2924330 A1 | 6/2009 |
| GB | 2051153 A | 1/1981 |
| JP | H0332677 U | 3/1991 |
| JP | H05237128 A | 9/1993 |
| JP | H09137380 A | 5/1997 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 0181667 A1 | 11/2001 |
| WO | 0207648 A1 | 1/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005105172 A1 | 11/2005 |

(56) References Cited

FOREIGN PATENT DOCUMENTS

| WO | 2006018552 A1 | 2/2006 |
|---|---|---|
| WO | 2006023444 A2 | 3/2006 |
| WO | 2007048099 A3 | 9/2010 |

OTHER PUBLICATIONS

Blondin, C. et al., "Inhibition of Complement Activation by Natural Sulfated Polysaccharides (Fucans) from Brown Seaweed," Molecular Immuol., Mar. 1994, pp. 247-253, 31(4).
Blondin, C. et al., "Relationships between chemical characteristics and anticomplementary activity of fucans," Biomaterials, Mar. 1996, pp. 597-603, 17(6).
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Canadian Office Action dated Jan. 16, 2017 in Canadian Patent Application No. 2,772,114, 4 pages.
Collins, R. et al., "Use of collagen film as a dural substitute: Preliminary animal studies," Journal of Biomedical Materials Research, Feb. 1991, pp. 267-276, vol. 25.
Ellouali, M. et al., "Antitumor Activity of Low Molecular Weight Fucans Extracted from Brown Seaweed *Ascophyllum nodosum*," Anticancer Res., Nov.-Dec. 1993, pp. 2011-2020, 12 (6A).
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Haroun-Bouhedja, F. et al., "Relationship between sulfate groups and biological activities of fucans," Thrombosis Res., Dec. 2000, pp. 453-459, 100(5).
Hirano, S. et al., "The blood biocompatibility of chitosan and N-acylchitosans," J. Biomed. Mater. Res., Apr. 1985, 413-417, 19.
International Search Report for Application No. PCT/EP2010/063062 dated Dec. 17, 2010.
Junge, K. et al., "Functional and Morphologic Properties of a Modified Mesh for Inguinal Hernia Repair," World J. Surg., Sep. 2002, pp. 1472-1480, 26.
Kanabar, V. et al., "Some structural determinants of the antiproliferative effect of heparin-like molecules on human airway smooth muscle," Br. J. Pharmacol., Oct. 2005, pp. 370-777, 146(3).
Klinge, U. et al., "Foreign Body Reaction to Meshes Used for the Repair of Abdominal Wall Hernias," Eur J. Surg, Sep. 1999, pp. 665-673, 165.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Langenbech, M. R. et al., "Comparison of biomaterials in the early postoperative period," Surg Endosc., May 2003, pp. 1105-1109, 17 (7).
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Malette, W. G. et al., "Chitosan, A New Hemostatic," Ann Th. Surg., Jul. 1983, pp. 55-58, 36.
Muzzarelli, R .et al., "Reconstruction of parodontal tissue with chitosan," Biomaterials, Nov. 1989, pp. 598-604, 10.
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Preliminary Search Report from French Patent Office dated Dec. 20, 2006, 3 pages.
Prokop, A. et al., "Water Soluble Polymers for Immunoisolation I: Complex Coacevation and Cytotoxicity," Advances in Polymer Science, Jul. 1998, pp. 1-51, 136.
Rao, B. et al., "Use of chitosan as a biomaterial: Studies on its safety and hemostatic potential," J. Biomed. Mater. Res., Jan. 1997, pp. 21-28, 34.
Rosen, M. et al., "Laparoscopic component separation in the single-stage treatment of infected abdominal wall prosthetic removal," Hernia, 2007, pp. 435-440, 11, published online Jul. 2007.
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220, 18(2).
Strand, S. et al., "Screening of Chitosans and Conditions for Bacterial Flocculation," Biomacromolecules, Mar. 2001, 126-133, 2.
Varum, K. et al., "In vitro degradation rates of partially N-acetylated chitosans in human serum," Carbohydrate Research, Mar. 1997, pp. 99-101, 299.
Welty, G. et al., "Functional impairment and complaints following incisional hernia repair with different polypropylene meshes," Hernia, Aug. 2001; pp. 142-147, 5.
Zvyagintseva, T. et al., "Inhibition of complement activation by water-soluble polysaccharides of some far-eastern brown seaweeds," Comparative Biochem and Physiol, Jul. 2000, pp. 209-215, 126(3).

* cited by examiner

ABDOMEN
GRIPPING FABRIC COATED WITH A BIORESORBABLE IMPENETRABLE LAYER

CROSS-REFERENCE TO RELATED APPLICATIONS

This application is a divisional of U.S. patent application Ser. No. 13/393,994, filed on Mar. 2, 2012, which is a National Stage Application of PCT/EP2010/0693062 under 35 USC § 371 (a) filed on Sep. 6, 2010, which claims benefit of and priority to French Patent Application No. 0956039 filed Sep. 4, 2009, the disclosures of each of the above-identified applications are hereby incorporated by reference in their entirety.

The present invention relates to a prosthetic fabric equipped with barbs, said fabric being covered, at least partially, with a bioresorbable microporous layer. Such a fabric can particularly be used for producing wall-reinforcing prostheses intended to be introduced into a patient by coelioscopy.

Wall-reinforcing prostheses, for example prostheses for reinforcing the abdominal wall, are widely used in the surgical field. These prostheses are intended for treating hernias by temporarily or permanently filling a tissue defect. These prostheses are generally made from a biocompatible prosthetic fabric and may have several shapes, rectangular, round, oval, depending on the anatomical structure to which they must be fitted. Some of these prostheses are made from entirely bioresorbable yarns and are intended to disappear after having carried out their reinforcing role until cell colonization takes place and tissue rehabilitation takes over. Other prostheses comprise non-bioresorbable yarns and are intended to remain permanently in the body of the patient.

Some of these prostheses are made from a knit, weaving or else non-woven arrangement of yarns, comprising barbed naps that protrude outwards from one face of the prosthesis: these barbs constitute hooks capable of being fastened either to another prosthetic fabric, belonging to the same prosthesis or not, or directly to the biological tissues, such as for example the abdominal wall. Certain prostheses may also comprise barbs on each of their two faces.

Furthermore, for the sake of minimizing the traumatisms subsequent to any surgical operation, patients are increasingly often operated on via coelioscopic surgery when the type of operation carried out permits it. Coelioscopic surgery requires only very small incisions, through which a trocar is passed, within which the prosthesis is conveyed to the implantation site. Thus open surgery is avoided and the patient can leave hospital rapidly. Coelioscopic surgery is particularly popular in surgical operations carried out in the abdomen, such as for example the treatment of hernias.

However, the trocars used in coelioscopic surgery generally have a relatively small calibrated diameter, which may vary, for example, from 5 to 15 mm, in order to reduce the size of the incision made as much as possible. The prosthesis must therefore be conveyed within a channel of reduced diameter and it must then be deployed to the implantation site.

In order to carry out this step, the prosthesis is generally wound around on itself in order to make it slide in the channel of the trocar or directly introduced by force. However, when the prosthetic fabric forming the prosthesis comprises barbs on one face, it may happen that these barbs become entangled in the body of the fabric and upset the subsequent deployment of the prosthesis at the implantation site. Furthermore, due to the fact that they are not protected, the barbs may be damaged during the unrolling of the prosthesis or during its transportation through the trocar to the implantation site.

Thus, there remains the need for a prosthetic fabric comprising barbed naps, that can be used for manufacturing prostheses, such as for example abdominal wall reinforcements, capable of being conveyed within a channel such as that of a trocar, without damaging the barbs, and capable of being completely deployed, and preferably in an easy manner, once it has reached the implantation site in the body of the patient.

The present invention aims to remedy such a need.

A first aspect of the present invention relates to a prosthetic fabric comprising an arrangement of yarns that define at least first and second opposite faces for said fabric, said fabric comprising on at least said first face one or more barbs that protrude outwards relative to said first face, said fabric being covered, at least partly, on said second face with a layer made of a bioresorbable material, the outer surface of said layer being impenetrable by said barbs, characterized in that the barbs are, in addition, covered with a coating made of a water-soluble material.

Another aspect of the invention relates to a prosthetic fabric comprising an arrangement of yarns that define at least first and second opposite faces for said fabric, said fabric comprising on at least said first face one or more barbs that protrude outwards relative to said first face, said fabric being covered, at least partly, on said second face with a layer made of a bioresorbable material, the outer surface of said layer being impenetrable by said barbs, said impenetrable layer comprising at least a bioactive agent.

In the present application, by the fact that the outer surface of the layer is impenetrable to said barbs, it is understood that the outer surface of the layer is either non porous or is provided with micropores the size of which is less than the size of the barbs so that the barbs are not allowed to penetrate within the layer of bioresorbable material. In other words, when the barbs come in contact with the outer surface of the layer of bioresorbable material, for example when the fabric is rolled upon itself, then the barbs are stopped by the outer surface of the layer of bioresorbable material and do not enter this layer. As a consequence, as long as the layer of bioresorbable material is not bioresorbed, the barbs can not get entangled in the fabric, even if the fabric is rolled upon itself.

The impenetrable layer according to the prevent invention may be a microporous layer.

Another aspect of the present invention relates to a prosthetic fabric comprising an arrangement of yarns that define at least first and second opposite faces for said fabric, said fabric comprising on at least said first face one or more barbs that protrude outwards relative to said first face, said fabric being covered, at least partly, on said second face with a microporous layer made of a bioresorbable material characterized in that the barbs are, in addition, covered with a coating made of a water-soluble material.

In the present application, the expression "microporous layer" is understood to mean a layer having an outer surface which is free of pores with a size strictly greater than 300 μm, in other words free of pores for which at least one diameter is strictly greater than 300 μm. Thus, the outer surface of the microporous layer of the fabric according to the invention may not comprise pores at all or else may comprise pores whose average size is of the order of one nanometre; alternatively, the outer surface of the microporous layer of the fabric according to the invention comprises pores whose maximum size is less than or equal to 300 µm, for example less than or equal to 150 µm.

In the case where the outer surface of the microporous layer of the fabric according to the invention comprises pores, the average size of these pores may preferably vary from 10 to 150 µm, for example from 20 to 150 µm: in such a case, the microporous layer of the fabric according to the invention may also comprise such pores in its thickness: such a microporous layer can promote cell colonization.

In the case where the outer surface of the microporous layer of the fabric according to the invention does not comprise pores, it preferably has a substantially smooth outer surface: in such a case the microporous layer of the fabric according to the invention may form a temporary barrier to macromolecules and to cells. For example, the non-porous layer may form a film.

In the present application, the term "biocompatible", is understood to mean that the materials having this property can be implanted in the body of animals or of man.

In the present application, the term "bioresorbable" or "biodegradable" is understood to mean that the materials having this property are absorbed and/or degraded by the tissues or washed from the implantation site and disappear in vivo after a certain time, which may vary, for example, from a few hours to a few months, depending on the chemical nature of the materials.

Due to the presence of the impenetrable, in particular microporous, layer, the prosthetic fabric according to the invention may be wound around on itself without the barbs becoming entangled in the body of the fabric, that is to say in the part of the fabric between the two opposite faces of the fabric. The impenetrable, in particular microporous, layer prevents the barbs of the prosthetic fabric from fastening to the fabric, especially when the fabric is wound around on itself in order to be inserted into a trocar. Thus, when the prosthetic fabric according to the invention is wound around on itself, the barbs are in contact with the impenetrable, in particular microporous, layer, in particular with the outer surface of the latter, and are not damaged. Furthermore, due to the fact that the barbs do not become entangled in the fabric, the prosthetic fabric according to the invention is capable of being completely deployed once it has reached the implantation site in the body of the patient.

In the present application, the impenetrable, in particular microporous, layer may also retard or prevent the tissue growth of the surrounding tissues, thus acting as a barrier to post-operative tissue adhesions and prevent the formation of undesired scar tissue.

In one embodiment of the invention, the impenetrable, in particular microporous, layer is continuous, and completely covers said second face.

In one embodiment of the invention, said bioresorbable material comprises at least one collagen compound.

The expression "collagen compound" is understood in the sense of the present application to mean collagen which has at least partially lost its helical structure by heating or by any other method, or gelatin. The term "gelatin" here includes commercial gelatin made from collagen which has been denatured by heating and in which the chains have been at least partially hydrolysed and which has a molar mass of less than around 100 kDa.

In one embodiment of the invention, said collagen compound comprises oxidized collagen. Alternatively or in combination, said collagen compound comprises gelatin.

In one embodiment of the invention, said bioresorbable material comprises a hydrophilic macromolecular additive chosen from polyalkylene glycols, such as polyethylene glycol or polypropylene glycol, polysaccharides, such as starch, dextran and/or derivatives of cellulose, oxidized polysaccharides, mucopolysaccharides, and mixtures thereof. For example, said hydrophilic macromolecular additive is a polyethylene glycol having a molar mass of 4000 daltons (PEG 4000).

In embodiments of the invention, said bioresorbable material comprises at least one polyvinyl alcohol.

In embodiments of the invention, said bioresorbable material comprises at least one glycerol.

In embodiments of the invention, the impenetrable layer comprises at least one bioactive agent. The impenetrable layer may act as media for the release of one or more bioactive agents.

In embodiments of the invention, the barbs are, in addition, covered with a coating made of a water-soluble biocompatible material.

The expression "water-soluble material" is understood in the sense of the present application to mean a material capable of dissolving in an aqueous composition such as water or biological fluids, for example at ambient temperature, either approximately at a temperature of around 20 to 25° C., or at any higher temperature and in particular at the temperature of the human body, in other words at a temperature of around 37° C.

Preferably, the water-soluble material of the fabric according to the invention is in set or solid form at a temperature less than or equal to 35° C., when it is not in contact with an aqueous composition.

In general, the material that covers the barbs, due to its water-soluble nature, has a smooth surface at a temperature of less than or equal to 25° C.: thus, when a barb covered with water-soluble material comes into contact with another barb covered with water-soluble material, they slide over one another and do not put up any resistance.

Thus, in embodiments of the invention, the prosthetic fabric is covered, on its second face, with an impenetrable, for example microporous, layer made of a bioresorbable material and the barbs of its first face are covered with water-soluble material. When a prosthesis made of such a fabric is wound around on itself in order to make it slide into a trocar, the barbs are doubly protected: not only do they slide over the outer surface of the impenetrable, for example microporous, layer but they do not hook onto one another: they slide over one another and they are easily separated from one another as soon as the prosthesis is released from the walls of the trocar in the implantation site: the prosthesis is then easily deployed before all of the water-soluble material covering the barbs is completely dissolved.

When the fabric according to the invention is brought into contact with water or biological fluids, in particular at the temperature of the human body, i.e. around 37° C. at the implantation site, the material covering the barbs dissolves little by little and thus detaches from the barbs. The time necessary for the solubilization of all of the water-soluble material covering the barbs and the presence of the impenetrable, for example microporous, layer made of a bioresorbable material make it possible to deploy the prosthesis easily. Once the barbs are no longer covered, they can again play their role of fastening, either to another prosthetic fabric, or within a biological tissue, such as for example the abdominal wall.

Furthermore, this necessary solubilization time, of the order of a few seconds to a few minutes, also allows the surgeon to position the prosthesis, moving it if necessary, and this being easy since, as the water-soluble material is not yet completely dissolved, the barbs slide with respect to the surrounding tissues and do not yet fasten the prosthesis as they will do once they are completely free of the coating made of the water-soluble material.

In embodiments of the invention, said water-soluble material is biodegradable.

In embodiments, said water-soluble material is chosen from polyethylene glycols (PEGs), polyvinyl acetates (PVAcs), collagen, gelatin, polyglucuronic acid, hyaluronic acid, carboxymethyl cellulose, cellulose ethers, chitosan and mixtures thereof.

For example, said water-soluble material is a polyethylene glycol having a molar mass of less than or equal to 40 000 Da, preferably less than or equal to 20 000 Da. For example, said molar mass may vary from 1000 to 20 000 Da. The polyethylene glycols having such molar masses are particularly biodegradable.

In embodiments, said water-soluble material comprises at least one polyethylene glycol having a molar mass of around 1000 Da. Such a polyethylene glycol enables an improved solubilization.

In embodiments, said water-soluble material comprises at least one bioactive agent.

The impenetrable layer and/or the water-soluble material may act as media for the release of one or more bioactive agents.

In embodiments, both the impenetrable layer and the water-soluble material comprise each a bioactive agent. The bioactive agents of the impenetrable layer and of the water_soluble material may be identical or different. In embodiments, after implantation of the prosthetic fabric, the water-soluble material will be dissolved in the biological fluids before the entire bioresorption of the impenetrable layer. In consequence, such embodiments may be useful for releasing in the body of the patient one or several bioactive agents in a sequential manner: for example, a first bioactive agent initially present in the water-soluble material will be released rapidly together with the dissolution of the water-soluble material in the biological fluids, for a specific bioactive effect, and a second bioactive agent, initially present in the impenetrable layer, will be released later on and possibly during a longer time for a second bioactive effect. In case the same bioactive agent is present in both the water-soluble material and the impenetrable layer, then a first shock effect may be obtained with the dissolution of the water-soluble material, and then a more prolonged effect may be obtained during the progressive bioresorption of the impenetrable layer.

Another aspect of the present invention relates to a process for covering a prosthetic fabric comprising an arrangement of yarns that define first and second faces for said fabric, said fabric comprising, over at least said first face, one or more barbs that protrude outwards relative to said first face, characterized in that it comprises the following steps:
  a°) a solution comprising at least one bioresorbable material is prepared;
  b°) a layer of said solution is applied to an inert support; and
  c°) when said layer is at least partially gelled, said second face of the fabric is applied to said layer, and
  i) a composition is prepared that comprises at least one water-soluble biocompatible material in the liquid state; and
  ii) a layer of said composition is applied to said barbs, wherein steps i) and ii) are carried out in any order relative to steps a°) to c°).

Another aspect of the present invention relates to a process for covering a prosthetic fabric comprising an arrangement of yarns that define first and second faces for said fabric, said fabric comprising, over at least said first face, one or more barbs that protrude outwards relative to said first face, characterized in that it comprises the following steps:
  a°) a solution comprising at least one bioresorbable material and at least one bioactive agent is prepared;
  b°) a layer of said solution is applied to an inert support; and
  c°) when said layer is at least partially gelled, said second face of the fabric is applied to said layer.

In embodiments, during step c°), a second layer of solution is applied to the partially gelled layer, before the application of the second face of the fabric.

In another embodiment, during step c°), a layer of a second solution of bioresorbable material is applied to the partially gelled layer, before the application of the second face of the fabric, the composition of said second solution of bioresorbable material being different from the solution obtained in a°). For example, said second solution may comprise the same bioresorbable material as the solution obtained in a°) but in different proportions. Such an embodiment makes it possible to obtain a prosthetic fabric covered on its second face with a film having good elasticity properties.

In embodiments, the prosthetic fabric obtained in step c°) is freeze-dried for a duration ranging from 20 to 60 hours. Such an embodiment makes it possible, for example, to obtain a prosthetic fabric covered on its second face with a microporous layer having pores that have a size ranging, for example, from 20 to 120 μm.

In embodiments, the two steps i) and ii) below are added, steps i) and ii) being carried out in any order relative to steps a°) and c°) described above:
  i) a composition is prepared that comprises at least one water-soluble biocompatible material in the liquid state; and
  ii) a layer of said composition is applied to said barbs.

In one embodiment of the process according to the invention, step ii) is carried out using a roll. Thus, the composition is uniformly spread over the roll then onto the barbs over which the roll is applied.

Another aspect of the invention relates to a prosthesis for the treatment of hernias, characterized in that it is manufactured from a fabric as described above or from a fabric obtained by the process as described above.

The present invention will now be described in greater detail with the aid of the following description and appended figures in which.

Figure 1:
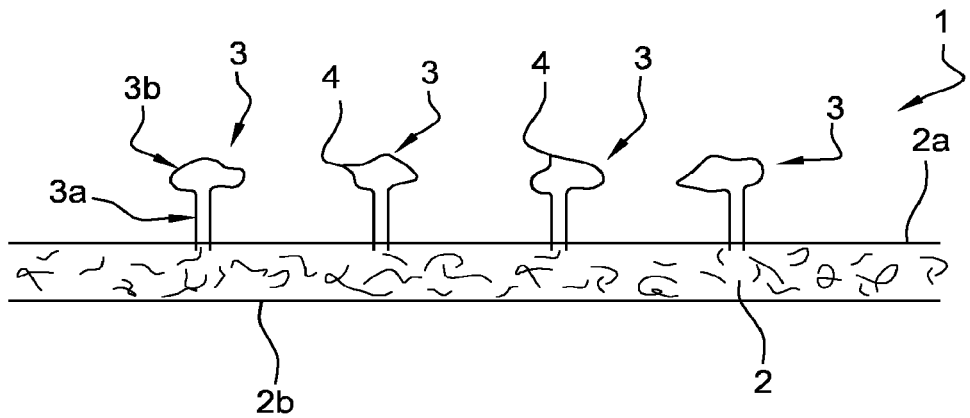
FIG. 1 is a schematic cross-sectional view of a prosthetic fabric with barbs from the prior art.

According to the present application, the expression "prosthetic fabric" is understood to mean any fabric obtained by an arrangement or an assembly of biocompatible yarns, fibres, filaments and/or multifilaments, such as a knitting, weaving, braiding or non-woven arrangement or assembly. The arrangement of the yarns of the fabric according to the invention defines at least two opposite faces, a first face and a second face. The prosthetic fabric according to the invention also comprises barbs that protrude from at least its first face. These barbs may protrude from said first face substantially perpendicular to the plane of said face or alternatively along one or more planes inclined relative to the plane of said face. These barbs are intended to function as fastening means, either by becoming entangled in one or more arrangements of yarns, fibres, filaments and/or multifilaments of another prosthetic fabric, or by anchoring to the biological tissues, such as for example an abdominal wall.

The barbs of the prosthetic fabric according to the invention may be formed from yarns, for example, hot-melt monofilament yarns directly resulting from the arrangement of yarns forming the fabric. Such fabrics and barbs and also their manufacturing process are, for example, described in applications WO 01/81667, DE 198 32 634 or else in U.S. Pat. Nos. 6,596,002, 5,254,133.

In such cases, for example, the barbs are formed from monofilament yarns made of polylactic acid.

Alternatively, the barbs of the prosthetic fabric according to the invention may be any hook produced from any biocompatible material, attached to the arrangement of yarns forming said fabric, whether these hooks were incorporated into said fabric during the manufacture (braiding, knitting, weaving, etc.) of said arrangement of yarns or were added afterwards.

Preferably, the barbs have the shape of a rod surmounted by a head: the average size of the heads of the barbs in general varies from 300 μm to 500 μm.

The yarns, or fibres or filaments and/or multifilaments forming the arrangement of yarns of the fabric according to the invention may be produced from any biodegradable or non-biodegradable biocompatible material. Thus, the biodegradable materials suitable for the yarns of the fabric of the present invention may be chosen from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers of these compounds and mixtures thereof. The non-biodegradable materials suitable for the yarns of the fabric of the present invention may be chosen from polyethylene terephthalate (PET), polyamides, aramids, expanded polytetrafluoroethylene, polyurethane, polyvinylidene difluoride (PVDF), polybutylesters, PEEK (polyetheretherketone), polyolefins (such as polyethylene or polypropylene), copper alloys, silver alloys, platinum, medical grades of steel such as medical grade stainless steel, and combinations thereof.

In order to prepare a fabric according to the invention, a prosthetic fabric is generally provided comprising an arrangement of yarns that define at least two faces for said fabric, said fabric comprising, on at least one of its faces, one or more barbs that protrude outwards relative to said face: such fabrics may be prepared, for example, as described in WO 01/81667.

Fabrics with barbs that are suitable for the present invention are also available commercially from the company Sofradim Production under the trade name Parietex® Progrip or else Parietene® Progrip.

The prosthetic fabric according to the invention is at least partly covered on its second face, that is to say on its face opposite the face comprising the barbs, with an impenetrable, for example microporous, layer made of a bioresorbable material. The impenetrable, for example microporous, layer of the fabric according to the invention is produced from a solution comprising said bioresorbable material.

Any natural or synthetic biocompatible and bioresorbable material may be used for preparing the impenetrable, for example microporous, layer. It is understood that any combination of natural and synthetic biocompatible and resorbable materials may be used. The techniques for forming the impenetrable, for example microporous, layers from such materials are known to a person skilled in the art, for example, non-limitingly, casting, moulding and similar techniques.

In the present application, synthetic materials may be used for preparing the impenetrable, for example microporous, layer of the fabric according to the invention. Examples of suitable synthetic materials include, non-limitingly, polylactic acid, polyglycolic acid, polyhydroxybutyrate acid, polyesters, polyethylene glycols, polyvinyl alcohols, polydioxanones, polycaprolactone, glycerols, polyamino acids, polytrimethylene carbonates, copolymers, block copolymers and/or homopolymers of these compounds, and mixtures thereof. As a synthetic material suitable for the present invention, mention may be made of the copolymer of polyvinyl alcohol (PVA) and of polyethylene glycol (PEG) sold under the trade name Kollicoat® IR by BASF.

In the present application, natural biological polymers may be used to form the impenetrable, for example microporous, layer of the fabric according to the invention. Suitable materials include, non-limitingly, collagen, gelatin, fibrin, fibrinogen, elastin, keratin, albumin, hydroxypropyl methyl cellulose, methyl cellulose, hydroxyethyl cellulose, hydroxypropyl cellulose, carboxyethyl cellulose, carboxymethyl cellulose, and mixtures thereof. In addition, the natural biological polymers may be combined with one or more of the synthetic materials described above in order to form the impenetrable, for example microporous, layer of the fabric according to the invention.

According to one embodiment of the invention, the bioresorbable material is chosen from collagen compounds, hydrophilic macromolecular compounds, polyvinyl alcohols, glycerols and mixtures thereof.

According to one embodiment of the fabric according to the invention, the bioresorbable material of the impenetrable, for example microporous, layer comprises at least one collagen compound.

In such an embodiment of the invention, an aqueous solution of a collagen compound is used to form the impenetrable, for example microporous, layer of the present invention. The expression "collagen compound" is understood in the sense of the present application to mean collagen which has at least partially lost its helical structure by heating or by any other method, or gelatin. The term "gelatin" here includes commercial gelatin made from collagen which has been denatured by heating and in which the chains have been at least partially hydrolysed and which has a molecular weight of less than around 100 kDa. The collagen compound used may be formed from hydrolysed collagen, composed of α chains and having a molecular weight close to around 100 kDa. In the context of the present invention, the expression "α chains" is understood to mean intact α chains or fragments produced by the loss of a small number of amino acids. The term "unhydrolysed" is understood here to mean that less than 10% of the collagen chains have a molecular weight of less than around 100 kDa. If heating is used to denature the helical structure of the collagen, the heating must be moderate and carried out under conditions arranged in order to avoid the degradation, by hydrolytic cleavage, of the gelatin thus formed.

The collagen possibly being used in the context of the present application may be of human or animal origin, and/or a mixture of the two, such as for example type I porcine or bovine collagens, type I or type III human collagens, and/or mixtures of the latter. Native collagen may be used, in acid solution or after conversion, in order to eliminate the telopeptides by pepsin digestion.

In one embodiment of the invention, the collagen compound comprises oxidized collagen. In order to obtain such an oxidized collagen, the collagen may be modified by oxidative cleavage using any technique known to a person skilled in the art including, non-limitingly, the use of periodic acid or one of its salts as described by Tardy et al. in U.S. Pat. No. 4,931,546, the whole of the content being incorporated therefore as reference. The technique described in this document comprises the mixing of collagen in acid solution with a solution of periodic acid or one of its salts at a concentration ranging from around $5×10^{-3}M$ to around $10^{-1}M$, and at a temperature ranging from around 10° C. to around 25° C., for around 10 minutes to around 72 hours. This method makes it possible to oxidize hydroxylysine and the sugars of collagen, thus creating reactive sites, aldehydes, without crosslinking the collagen thus converted. The oxidation of the collagen, thus described, makes it possible to obtain a controlled and moderate crosslinking in the collagen material, under suitable conditions. In other embodiments of the invention, the oxidative cleavage may be obtained by other means in order to obtain a controlled and moderate crosslinking, for example, but non-limitingly, β or γ irradiation. In other embodiments of the invention, the oxidative cleavage may be provided by other reactants that allow a controlled and moderate crosslinking, for example, and non-limitingly, to chemical reactants at appropriate, low and non-toxic doses.

In other embodiments of the invention, the degree of crosslinking of the collagen may be increased by any technique known to a person skilled in the art so as to adjust the degradation time of the impenetrable, for example microporous, layer as desired. The expression "moderate crosslinking" is understood in the sense of the present application to mean that the impenetrable, for example microporous, layer is at least 90% degraded (as measured by the residual weight) at the end of around one month after implantation. The expression "high crosslinking" is understood in the sense of the present application to mean that the impenetrable, for example microporous, layer is at least 90% degraded (as measured by the residual weight) at the end of around three months after implantation. The expression "very high crosslinking" is understood in the sense of the present application to mean that the impenetrable, for example microporous, layer is at least 90% degraded (as measured by the residual weight) at the end of around two years after implantation.

In the present application, a solution of oxidized collagen as defined above may be used to form the impenetrable, for example microporous, layer, having a collagen concentration ranging from around 5 g/l to around 50 g/l, preferably between around 10 g/l to around 35 g/l.

In the present application, the solution of oxidized collagen may be heated, for example at a temperature above 37° C. approximately, for example at a temperature ranging from around 40° C. to around 50° C., for at least around one hour, in order to at least partially denature the helical structure of the collagen. Other physical or chemical techniques for denaturing the collagen include, for example, non-limitingly, ultrasonic treatment or the addition of chaotropic agents.

In one embodiment of the invention, the collagen compound comprises gelatin. In such an embodiment, a gelatin solution as defined above may be used to form the impenetrable, for example microporous, layer, having a gelatin concentration ranging from around 5 g/l to around 50 g/l, preferably between around 25 g/l to around 35 g/l.

In one embodiment of the invention, the hydrophilic macromolecular compounds are chosen from polyalkylene glycols, such as polyethylene glycol or polypropylene glycol, polysaccharides, such as starch, dextran and/or derivatives of cellulose, oxidized polysaccharides, mucopolysaccharides, and mixtures thereof. For example, the hydrophilic macromolecular additive is a polyethylene glycol having a molar mass of 4000 daltons.

In one embodiment of the invention, one or more hydrophilic macromolecular compounds which are chemically inert with the collagen compound may be added to the solution in order to form the impenetrable, for example microporous, layer.

The macromolecular compound may have a molar mass ranging above around 3000 daltons, preferably between around 3000 and around 20,000 daltons. Suitable hydrophilic macromolecular compounds include, but in a non-limiting manner, polyalkylene glycols (such as polyethylene glycol, polypropylene glycol), polysaccharides (such as starch, dextran and/or derivatives of cellulose), oxidized polysaccharides, mucopolysaccharides, and mixtures thereof.

In the present application, polyethylene glycol 4000 (4000 corresponding to the molar mass) may be added as a hydrophilic macromolecular compound. The concentration of hydrophilic macromolecular compound may be from around 2 to 10 times lower than the concentration of the collagen compound in the solution for preparing the impenetrable, for example microporous, layer. Optionally, the hydrophilic macromolecular compound may be removed by diffusion through the impenetrable, for example microporous, layer in a few hours to a few days.

In one embodiment of the invention, the bioresorbable material comprises at least one glycerol. For example, the bioresorbable material comprises at least one collagen compound and at least one glycerol. For example, the bioresorbable material comprises at least one collagen compound, at least one glycerol and at least one hydrophilic macromolecular compound, for example polyethylene glycol 4000.

In the present application, the glycerol may be used in the solution of the collagen compound in order to form the impenetrable, for example microporous, layer. The glycerol concentration in the solution of the collagen compound may be from around 2 to around 10 times lower than the concentration of the collagen compound, preferably less than one third approximately of the concentration of the collagen compound in the solution for preparing the impenetrable, for example microporous, layer.

In the present application, the term "concentration" is understood to mean weight per volume concentrations.

In the present application, the initial concentrations, in the solution for preparing the impenetrable, for example microporous, layer, of the collagen compound, or of the hydrophilic macromolecular compound(s), in particular of polyethylene glycol 4000, and of the glycerol may range from around 2% to 10% for the collagen compound, from around 0.6% to 4% for the hydrophilic macromolecular compound(s) and from around 0.3% to around 2.5% for the glycerol, respectively.

The solution used to form the impenetrable, for example microporous, layer may be prepared by adding the collagen compound, the hydrophilic macromolecular compound(s) and the glycerol to water or to a water/alcohol, for example ethanol, mixture at a temperature ranging from around 30° C. to around 50° C. The solution may be neutralized to a neutral pH in order to avoid hydrolysing the collagen compound by heating and in order to obtain a film having a physiological pH while enabling the pre-crosslinking of the collagen compound if the mixture contains oxidized collagen as indicated above.

In one embodiment of the invention, the bioresorbable material comprises at least one polyvinyl alcohol.

In the present application, a solution of polyvinyl alcohol may be used to form the impenetrable, for example microporous, layer.

Polyvinyl alcohols suitable for the present application have, for example, properties that enable them to be bioresorbed in less than a few days.

Polyvinyl alcohols suitable for the present application have, for example, a degree of hydrolysis between around 80% and around 99%, preferably between around 90% and around 99%.

Polyvinyl alcohols suitable for the present application have, for example, a molar mass of less than around 200,000 daltons, preferably of less than around 50,000 daltons.

Polyvinyl alcohols suitable for the present application may be a mixture of polyvinyl alcohols having different characteristics, but corresponding to the preferences described above, in terms of degree of hydrolysis and molar masses.

In the present application, a solution of polyvinyl alcohol as defined above may be used to form the impenetrable, for example microporous, layer, having a polyvinyl alcohol concentration ranging from around 20 g/l to around 200 g/l, preferably between around 50 g/l to around 100 g/l.

In one embodiment of the invention, the bioresorbable material comprises at least one polyvinyl alcohol and at least one glycerol.

In the present application, the glycerol may be used in the polyvinyl alcohol solution in order to form the impenetrable, for example microporous, layer. The glycerol concentration in the polyvinyl alcohol solution may be from around 2 to around 10 times lower than the polyvinyl alcohol concentration, preferably less than one third approximately of the polyvinyl alcohol concentration.

In the present application, the impenetrable, for example microporous, layer made from polyvinyl alcohol is, for example, bioresorbed between around a few minutes and around a few days.

In the present application, the microporous layer may be obtained from a solution resulting from the mixture of the collagen compound and of polyvinyl alcohol.

In one embodiment of the invention, the bioresorbable material comprises at least one collagen compound and at least one polyvinyl alcohol.

In the present application, the polyvinyl alcohol concentration in the solution of the impenetrable, for example microporous, layer resulting from the mixture of the collagen compound and polyvinyl alcohol may be between 1 and 65% relative to the mass of the collagen compound, preferably between 20 and 50%.

In the present application, one or more hydrophilic macromolecular compounds which are chemically inert with the mixture of collagen compounds and polyvinyl alcohol may be added to the solution in order to form the impenetrable, for example microporous, layer.

The macromolecular compound may have a molar mass ranging above around 3000 daltons, preferably between around 3000 and around 20,000 daltons. Suitable hydrophilic macromolecular compounds include, but in a non-limiting manner, polyalkylene glycols (such as polyethylene glycol), polysaccharides (such as starch, dextran and/or cellulose derivatives), oxidized polysaccharides, mucopolysaccharides, and combinations of the latter.

In the present application, polyethylene glycol 4000 (4000 corresponding to the molar mass) may be added as a hydrophilic macromolecular compound. The concentration of the hydrophilic additives may be from around 2 to around 10 times lower than the total concentration of collagen compound and of polyvinyl alcohol. Optionally, the hydrophilic macromolecular compound may be removed by diffusion through the impenetrable, for example microporous, layer in a few hours to a few days.

Thus, in one embodiment of the invention, the bioresorbable material comprises at least one collagen compound, at least one polyvinyl alcohol and at least one hydrophilic macromolecular compound, for example polyethylene glycol 4000.

In the present application, the glycerol may be used in the solution of the mixture of collagen compound and polyvinyl alcohol in order to form the impenetrable, for example microporous, layer. The glycerol concentration in the solution of the mixture of collagen compound and polyvinyl alcohol may be from around 2 to around 10 times lower than the total concentration of the collagen compound and polyvinyl alcohol, preferably less than one third approximately of the total concentration of collagen component and polyvinyl alcohol.

Thus, in one embodiment of the invention, the bioresorbable material comprises at least one collagen compound, at least one polyvinyl alcohol and at least one glycerol. The bioresorbable material may also comprise copolymers of PVA and PEG sold under the trade name Kollicoat® IR by BASF.

The solution used to form the impenetrable, for example microporous, layer may be prepared by adding the collagen compound and the polyvinyl alcohol, the hydrophilic macromolecular additive(s), for example PEG 4000, the Kollicoat® IR and the glycerol to water or to a water/alcohol, for example ethanol, mixture at a temperature ranging from around 30° C. to around 50° C. The solution may be neutralized to a neutral pH in order to avoid hydrolysing the collagen compound by heating and in order to obtain a film having a physiological pH while enabling the pre-crosslinking of the collagen compound if the mixture contains oxidized collagen as indicated above.

In the present application, a bioactive agent may be added to the impenetrable, for example microporous, layer.

In the present application, the impenetrable, for example microporous, layer of the fabric according to the invention may act as a medium for the release of a bioactive agent.

In the present application, the expression "bioactive agent" is understood to mean a bioactive agent in its broadest sense, including any substance or mixture of substances which have a clinical use. Therefore, the bioactive agents may or may not have a pharmacological activity per se such as for example, non-limitingly, pigments or colorants. Alternatively, a bioactive agent may be any agent that provides a therapeutic or prophylactic effect, a compound that affects or participates in tissue growth, in cell growth, in cell differentiation, a compound that displays adhesion-preventing properties, a compound capable of causing a biological action such as an immune response or capable of playing a role in one or more biological processes. It is considered that the bioactive agent may be included in the solution that forms the impenetrable, for example microporous, layer, in any suitable form such as in the form of powder, liquid, gels and related forms.

The expression "bioactive agent" used here is used in its broadest sense and includes any substance or mixture of substances which have a clinical use. Consequently, the bioactive agents may or may not have a pharmacological activity per se such as for example pigments. Alternatively, a bioactive agent may be any agent that has a prophylactic or therapeutic effect, a compound which affects or participates in tissue growth, cell growth, and/or cell differentiation; a compound which may be capable of causing a biological action such as an immune respnse; or a compound which could play another role in one or more biological processes.

Any agent which can produce therapeutic benefits such as for example tissue repair or cell proliferation, which limits the risk of sepsis, may be added to the impenetrable, for example microporous, layer of the prosthetic fabric according to the invention. Such agents include, for example, fucans, dextrans, derivatives of dextrans, carrageenans, alginate, hyaluronic acid, keratin sulphate, keratan sulphate, dermatan sulphate, chitin, chitosan, combinations of these compounds and of their derivatives. For example, chitosan may be added to the impenetrable, for example microporous, layer of the prosthetic fabric according to the invention: chitosan is biodegradable, has good biocompatibility, has demonstrated haemostatic and bacteriostatic properties, and it also plays an important role in cell proliferation and tissue regeneration.

Examples of classes of bioactive agents which may be used according to the present application include antimicrobials, analgesics, adhesion-preventing agents, antipyretics, anaesthetics, anticonvulsants, antihistamines, anti-inflammatories, cardiovascular drugs, diagnostic agents, sympathomimetics, cholinornimetics, antimuscarinics, antispasmodics, hormones, growth factors, muscle relaxants, adrenergic antagonists, antineoplastics, immunogenic agents, immunosuppressors, digestive drugs, diuretics, steroids, lipids, narcotics, lipopolysaccharides, polysaccharides, polypeptides, proteins, hormones, enzymes and combinations thereof.

Antimicrobial agents suitable for the present invention may be included among quaternary amines (for example, triclosan also known under the name 2,4,4'-trichloro-2'-hydroxydiphenyl ether, or diallyldimethylammonium chloride also known as DADMAC, chlorhexidine and its salts (i.e. chlorhexidine acetate, chlorhexidine gluconate, chlorhexidine hydrochloride and chlorhexidine sulphate), silver and its salts (i.e. silver acetate, silver benzoate, silver carbonate, silver citrate, silver iodate, silver iodide, silver lactate, silver laurate, silver nitrate, silver oxide, silver palmitate, silver protein complex and silver sulphadiazine), polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol-9, fusidic acid, cephalosporines, and combinations thereof. Antimicrobial proteins and peptides (i.e. bovine lactoferrin and lactoferricine B) may also be suitable as a bioactive agent according to the present application.

Other bioactive agents suitable for the present invention may be chosen from local anaesthetics; antisteroidal agents; parasympathomimetic agents; psychotherapeutic agents; tranquilizers; decongestants; hypnotic sedatives; steroids; sulphonamides; sympathomimetic agents; vaccines; vitamins; antimalarial drugs; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, D-propoxyphene and the like; opioid receptor antagonists such as naltrexone and naloxone; anti-cancer agents; anti-convulsants; anti-emetics; antihistamines; anti-inflammatory agents such as hormones (i.e. hydrocortisone, prednisolone, prednisone), non-hormonal agents (i.e. allopurinol, indomethacin, phenylbutazone and the like; prostaglandins and cytotoxic drugs; ostrogens; antibacterials; antibiotics; anti-fungals; anti-virals; anticoagulants; anticonvulsants; antidepressants; antihistamines; and immunological agents.

Other examples of bioactive biological agents suitable for the present invention include viruses and cells, peptides, polypeptides and proteins, analogues, muteins, and/or active fragments of these compounds, such as immunoglobulins, antibodies, beta-glycans, cytokines (e.g. lymphokines, monokines, chemokines), blood coagulation factors, haemopoietic factors, interleukins (IL-2, IL-3, IL-4, IL-6), interferons ([beta]-IFN, [alpha]-IFN and [gamma]-IFN), erythropoietin, nucleases, TNFs (tumor necrosis factors), CSFs (colony stimulating factors) (e.g. GCSF, GM-CSF, MCSF), insulin, anti-tumor agents and tumor suppressors, blood proteins, gonadotropins (e.g. FSH, LH, CG, etc.), hormones and hormone analogues (e.g. growth hormone), vaccines (e.g. tumour antigens, bacteria and viral antigens); somatostatin; antigens; blood coagulation factors; growth factors (e.g. nerve growth factor, insulin-like growth factor); protein inhibitors, protein antagonists and protein agonists; nucleic acids, such as antisense DNA and RNA molecules; oligonucleotides; and ribozymes.

In the present application, the impenetrable, for example microporous, layer may be prepared by first casting a solution of the bioresorbable material, such as for example, the collagen compound or the polyvinyl alcohol, intended to form said layer, and optionally containing the hydrophilic macromolecular compound(s) and glycerol and a bioactive agent, on a suitable and substantially flat inert support and by uniformly distributing the solution.

In the present application, a support is said to be inert if it does not react with the compounds of the solution of bioresorbable material as described above for the preparation of the impenetrable, for example microporous, layer of the fabric according to the invention and if it is not involved in the possible crosslinking processes. The inert supports suitable for the present invention may be made from hydrophobic materials such as for example, non-limitingly, polyvinyl chloride (PVC), polystyrene, or a material which may be detached and which will remain slightly adhesive and which may be easily separated from the fabric according to the invention at the moment of its surgical use.

In the present application, the inert support may consist of a film of polyvinyl chloride (PVC), onto which the solution of the impenetrable, for example microporous, layer is cast, the PVC being inert with respect to the bioresorbable material used for the impenetrable, for example microporous, layer of the fabric according to the invention.

In the present application, the density of the thin layer initially deposited in the form of solution on the inert support may be around 0.1 g of solution per cm² to around 0.3 g per cm². The solution of the impenetrable, for example microporous, layer may be cast at a temperature ranging from around 4° C. to around 30° C., preferably from around 18° C. to around 25° C. Once applied to the inert support, the solution of the impenetrable, for example microporous, layer is left under laminar flow until a gel is formed, until the solution is no longer fluid, for around 5 minutes to around 60 minutes. The gelling results from the cooling of the solution of the impenetrable, for example microporous, layer, for example when it contains collagen.

The second face, that is to say the one that does not comprise the barbs, of the prosthetic fabric is then applied to the at least partially gelled solution of the impenetrable, for example microporous, layer. Optionally, it is possible to apply a light pressure to the prosthetic fabric. This pressure must be light enough not to cause significant breaking of the portion of the layer of gelled solution in contact with the support, so as to maintain the integrity and continuity of the impenetrable, for example microporous, layer over its entire surface and to preferably cover the whole of the second face of the prosthetic fabric.

In the present application, before applying the prosthetic fabric, a second layer of solution may also be poured over the first. In one embodiment of the invention, the components of the solution used for the second layer are identical to those used for the first layer so as to obtain, at the end of the process, one and the same impenetrable, for example microporous layer. The density of the second thin layer deposited in the form of solution on the first layer may be around 0.1 g of solution per cm² to around 0.3 g per cm². The solution of the second layer may be cast as a temperature ranging from around 4° C. to around 30° C., for example from around 18° C. to around 25° C. Once applied to the support, the solution of the second microporous layer is left under laminar flow until a gel forms, until the solution is no longer fluid, for around 5 minutes to around 60 minutes. The gelling results from the cooling of the solution when it contains collagen. The prosthetic fabric is then applied to the gelled solution as indicated above in the context of the casting of a single thin layer.

In the present invention, the prosthetic fabric covered with the partially gelled impenetrable, for example microporous, layer may be dried in order to carry out the complete gelling of the impenetrable, for example microporous, layer. When the solution of the impenetrable, for example microporous, layer comprises oxidized collagen, the collagen is crosslinked during the drying process at a temperature of around 4° C. to around 35° C., preferably from around 18° C. to around 30° C. The whole assembly is dried under a sterile air flow.

After drying, the prosthetic fabric covered according to the invention may be separated from the inert support, cut to a defined size, if necessary, in order to manufacture a prosthesis, then packaged and sterilized using conventional techniques, such as for example, but non-limitingly, β irradiation (electronic irradiation), γ irradiation (irradiation with radioactive cobalt) or ethylene oxide treatment.

In embodiments of the invention, the barbs of the prosthetic fabric may be covered with a water-soluble material, before, during or after the process for covering the second face with the impenetrable, for example microporous, layer made of bioresorbable material.

In one embodiment, said water-soluble material is chosen from polyethylene glycols (PEGs), polyvinyl acetates (PVAcs), gelatin, polyglucuronic acid, hyaluronic acid, carboxymethyl cellulose, cellulose ethers, chitosan and mixtures thereof.

For example, said water-soluble material is a polyethylene glycol having a molar mass of less than or equal to 40 000 Da, preferably less than or equal to 20 000 Da. For example, said molar mass may vary from 1000 to 20 000 Da. The polyethylene glycols having such molar masses are particularly biodegradable.

In one embodiment, said water-soluble material comprises at least one polyethylene glycol having a molar mass of around 1000 Da. Such a polyethylene glycol permits an improved solubilization.

In embodiments, the water-soluble material comprises at least one bioactive agent. The bioactive agents that may be present in the water-soluble material may be chosen among the bioactive agents described above for the impenetrable layer.

Thus, in embodiments of the process according to the invention, the two steps i) and ii) below are added, steps i) and ii) being carried out in any order relative to steps a°) to c°) described above:

i) a composition is prepared that comprises at least one water-soluble biocompatible material in the liquid state; and ii) a layer of said composition is applied to said barbs.

The composition comprising the water-soluble biocompatible material in the liquid state may be in liquid, viscous or else pasty form. For example, the composition has a consistency that enables it to be spread over the barbs, for example using a brush or else a roll, or that enables the barbs to be immersed within it. In one embodiment of the process according to the invention, step ii) is carried out using a roll. Thus, the composition is uniformly spread over the roll then onto the barbs over which the roll is applied.

In one embodiment of the process according to the invention, said composition is obtained by solubilization of said water-soluble material in water, optionally by heating said composition at the melting point of said water-soluble material.

In one such embodiment, once the layer of composition is applied to the barbs, the composition is left to dry, and optionally cool, until the layer of water-soluble material covering the barbs is in the set state, that is to say solid state.

In another embodiment of the process according to the invention, said composition is obtained by heating said water-soluble material alone, at a temperature above the melting point of said water-soluble material. In such an embodiment, once the layer of composition is applied to the barbs, the composition is left to cool until the layer of water-soluble material covering the barbs is in the set state, that is to say solid state.

In the present application, when the prosthetic fabric is obtained from materials that are sensitive to hydrolysis such as polyglycolic acid or polylactic acid, it is packaged under conditions that are sufficiently low in moisture in order to prevent its degradation during storage.

The prosthetic fabrics of the present invention are stable at ambient temperature. The thickness of the impenetrable, for example microporous, layer may be less than around 150 µm, preferably between around 30 µm and around 100 µm. The prosthetic fabrics of the present invention may be produced at a predetermined size or be produced in large dimensions in order to be able to be cut therefore to suitable sizes for the applications envisaged, for example manufacture of prostheses.

Such prostheses may be implanted using open surgery or laparoscopic surgery. When implanted by laparoscopic surgery, the prosthesis must be wound around itself, before its insertion into the trocar. The impenetrable, for example microporous, layer of the prosthetic fabric according to the invention prevents the barbs from fastening to the prosthetic fabric during the transport of the prosthesis through the trocar and its deployment at the implantation site.

Thus, when the surgeon wishes to implant a prosthesis formed from a fabric according to the invention, he can easily wind this prosthesis around itself by folding the face provided with covered barbs towards the inside or towards the outside. In both cases, during this winding, the barbs come into contact with the impenetrable, for example microporous, layer, in particular against its outer gelled surface which may be substantially smooth, against which they are stopped: thus, the barbs do not penetrate into the body of the fabric and they do not become entangled with the arrangement of yarns constituting the fabric. Furthermore, the barbs are protected from rubbing against the walls of the trocar or against any other exterior element of the environment.

Once the prosthesis is conveyed to the implantation site via the trocar, the prosthesis can be unwound and deployed easily since the barbs slide over the impenetrable, for example microporous, layer and do not put up any resistance to the deployment of the prosthesis.

The prosthesis is deployed and the impenetrable, for example microporous, layer comes, little by little, into contact with the surrounding biological tissues where it is gradually bioresorbed. The prosthesis may be fastened, either to another fabric, or to a biological wall, using the barbs, the latter not having been subjected to any damage during the transport of the prosthesis in the channel of the trocar and having retained their coupling properties. In embodiments where the barbs are covered by a water-soluble material, the barbs may be used to fasten the prosthetic fabric to another fabric or to a biological wall once the water-soluble material has dissolved.

The prosthesis of the present application may maintain all the unique and original properties of the barbed prosthetic fabric, such as its use in the reinforcement and repair of soft tissues and its attachment to the tissues to be reinforced via the barbs, even after it has been transported through a trocar and deployed, in laparoscopic surgery.

The following examples illustrate the invention.

EXAMPLE 1A

A prosthetic fabric, having a size of 15×10 cm$^2$ and comprising barbs as described in WO 01/81667 is provided. The barbs are produced from a monofilament yarn made of polylactic acid (PLA).

A schematic representation of a cross section of such a fabric is given in FIG. 1: the fabric 1 is formed from an arrangement 2 of yarns that define two opposite faces 2a and 2b. The fabric 1 comprises, on its first face 2a, barbs 3 that protrude from this face. Each barb 3 is equipped with a shaft 3a and a head 3b. As it appears in this FIG. 1, the heads 3a of the barbs have asperities 4 that contribute to the coupling and gripping properties of the barbs. The heads 3a of the barbs have, for example, a size ranging from to 300 to 500 μm.

A microporous layer, in the form of a film comprising oxidized collagen, is combined with this prosthetic fabric on the face 2b, the face opposite the face bearing the barbs, in the following manner:

1°) Preparation of the Solution of Bioresorbable Material in Order to Form the Microporous Layer:

The collagen used is type I porcine collagen, extracted from pork skin by solubilization at acid pH or by pepsin digestion, and purified by saline precipitation according to known techniques.

Preferably, the dry collagen fibres are obtained by precipitation of an acid solution of collagen by addition of NaCl, then the washing and the drying of the precipitate are carried out with aqueous solutions of acetone having an acetone concentration increasing from 80% to 100%.

Prepared from these collagen fibres is a 3% w/v collagen solution which is oxidized by periodic acid at the final concentration of 8 mM, at ambient temperature, according to Example 4 of document U.S. Pat. No. 6,596,304.

A sterile concentrated solution of PEG 4000 (polyethylene glycol having a molar mass of 4000 daltons, for example sold by Fluka under the trade name PEG 4000) and of glycerol (also sold by Fluka) is added to the oxidized collagen solution at the concentration of 3% w/v, so as to obtain a mixture containing PEG 4000 at the final concentration of 1% w/v and glycerol at the final concentration of 0.6% w/v. The pH of the solution is adjusted to 7.0 by adding a concentrated sodium hydroxide solution. The volume of the solution is then topped up with sterile water so as to obtain final concentrations of oxidized collagen, of PEG 4000 and of glycerol of 2.7% w/v, 0.9% w/v and 0.54% w/v, respectively.

2°) Covering Face 2b of the Prosthetic Fabric:

A portion of the solution obtained in 1°) is spread so as to form a thin first layer with a density of 0.095 g/cm$^2$ over a flat hydrophobic inert support made of PVC or of polystyrene.

The surface of the first layer is then exposed to a flow of sterile air at ambient temperature, for between 5 and 60 minutes, in order to allow the solution to gel. The remaining solution is diluted to the concentration of 2% w/v with sterile water, then to the concentration of 1.75% with absolute ethanol. This solution is spread so as to form a thin second layer with a density of 0.045 g/cm$^2$ and is applied to the first layer.

The surface of the second layer is again exposed to a flow of sterile air at ambient temperature, for between 5 and 60 minutes. The prosthetic fabric is then applied gently to the gelled layer of the solution obtained in 1°) formed from the first and second layers above. The whole assembly is exposed to a flow of sterile air, at ambient temperature, until complete evaporation is achieved, in around 18 hours.

A barbed prosthetic fabric is obtained which is covered on its face that does not comprise the barbs with a microporous layer in the form of a continuous film. The microporous layer is continuous and completely covers said second face.

The relative concentrations of collagen, of PEG and of glycerol are 3/1/0.6, w/w/w, in the microporous layer, after drying.

The prosthetic fabric thus covered on its second face with the microporous layer is then detached from the inert support. In this example, the film forming the microporous layer (itself formed from the first and second layers above) is substantially free of pores and its outer surface is substantially smooth.

EXAMPLE 1B

A covered prosthetic fabric is manufactured in the same manner as in Example 1A above, except that a bioactive agent, is added to the solution prepared in Example 1A 1°).

Figure 2:
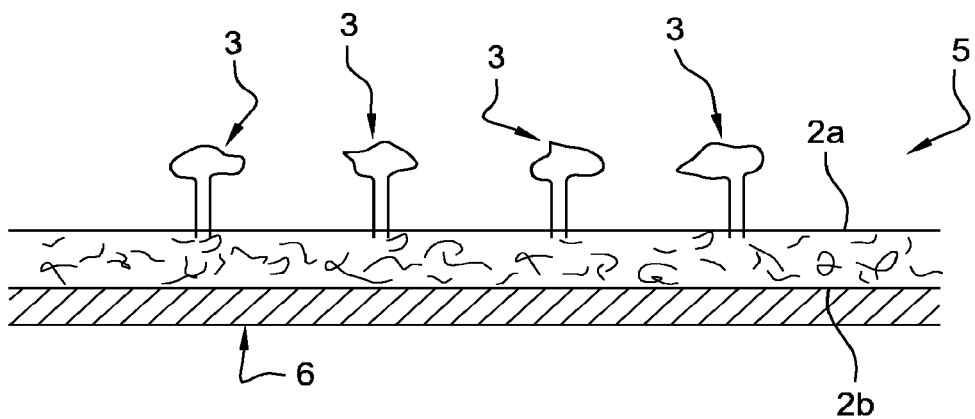
FIG. 2 is a schematic cross-sectional view of a prosthetic fabric according to the invention.

A schematic representation of a cross section of such a fabric 5 according to the invention is given in FIG. 2: the prosthetic fabric 5 according to the invention comprises barbs 3 on its first face 2a. As can be seen in FIG. 2, its second face 2b is covered with the smooth and microporous layer in the form of a film 6, as described above. Consequently, when the prosthetic fabric 5 obtained is wound around itself, the barbs 3 are brought into contact with the smooth surface of the microporous layer 6 and they do not become entangled in the body of the fabric, thus enabling an easier subsequent deployment of the fabric.

Moreover, the covered prosthetic fabric of the present example allows releasing a bioactive agent once the prosthetic fabric is implanted.

It is possible to manufacture prostheses for the treatment of hernias from the barbed fabric coated with a microporous layer as described in the present example, by cutting a rectangular or round shape, or a shape suitable for the anatomy of the organ to be treated, from said fabric.

The barbed fabric, coated with a microporous layer based on collagen, PEG 4000, glycerol and a bioactive agent as described in the present example, is particularly suitable for the manufacture of prostheses for the treatment of hernias via a coelioscopic technique. Indeed, such prostheses may be wound around themselves, barbs on the inside and/or on the outside and be conveyed in this manner into the channel of a trocar to the implantation site without risk of damaging the barbs. Furthermore, due to the presence of the microporous layer, the barbs, in particular the heads of these barbs, do not become entangled in the body of the fabric and do not hinder the deployment of the prosthesis once it is released from the trocar at the implantation site: once the prosthesis is unwound, the barbs, due to their coupling properties, may be used to fasten the prosthesis in the manner desired by the surgeon.

The prosthetic fabric covered as described above may be packed in a sterile double bag. It may be sterilized, preferably, by γ irradiation, at a dose ranging from 25 to 45 kGy. After sterilization, it is heated in an oven at 50° C. for around 48 hours. It is then stored at ambient temperature until it is used.

EXAMPLE 1C

Covering the Barbs of the Prosthetic Fabric of Example 1A with a Water Soluble Material:

A prosthetic fabric as obtained in Example 1A is provided before being packed. The barbs of the fabric are covered with a coating made of a water-soluble material, for example according to the following method:

5 g of polyethylene glycol having a molar mass of 4000 (PEG 4000 from FLUKA) the melting point of which is between 53° C. and 59° C., is heated at 60° C. in order to obtain a homogeneous liquid. Alternatively, the polyethylene glycol of molar mass 4000 could be replaced by a mixture of polyethylene glycols having molar masses of 1000, 2000 and 4000 respectively.

The barbs of the prosthetic fabric are coated with the PEG 4000 in the liquid state using a brush or by immersing the barbs in the liquid PEG 4000 composition.

For example, if a brush is used, and as a function of the viscosity of the PEG 4000 composition, the coating may be carried out by several successive passes of brushes over the barbs.

The thus covered fabric is then left to cool at ambient temperature (at around 20° C.). The PEG 4000 composition sets and coats the barbs, covering them with a smooth solid coating.

Figure 4:
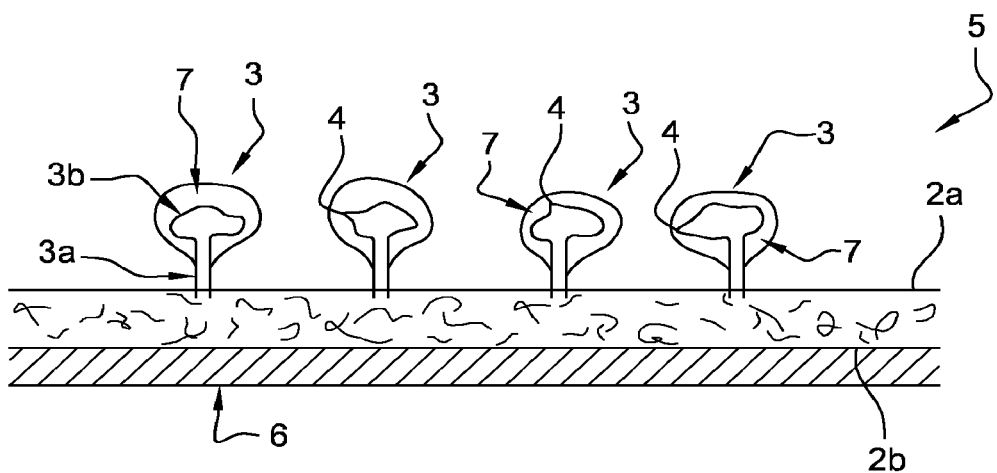
FIG. 4 is a cross-sectional schematic view of another embodiment of a prosthetic fabric according to the invention.

A schematic representation of a cross section of such a fabric 5 according to the invention, the second face of which is covered with a microporous layer 6 made of a bioresorbable material (as described in Example 1A above) and the barbs of which are covered with a water-soluble material, is given in FIG. 4: the prosthetic fabric 5 according to the invention comprises barbs 3 coated with a water-soluble material, in the form of a solid layer 7 in the example represented. The solid layer 7 of water-soluble material, namely polyethylene glycol having a molecular weight of 4000 in the present example, completely coats the head 3a of each barb 3 and also a portion of the shaft 3a. As can clearly be seen in FIG. 4, the surface of the layer 7 is smooth and the heads 3b of the barbs 3 no longer have asperities 4 accessible to any other fabric.

Thus, the coating of the barbs with PEG 4000 reduces the coupling of the fabric and facilitates its handling.

It is possible to manufacture prostheses for the treatment of hernias from the fabric with barbs coated with polyethylene glycol as described in the present example, by cutting a rectangular or round shape, or a shape suitable for the anatomy of the organ to be treated, from said fabric.

The fabric as described in the present example is particularly suitable for the manufacture of prostheses for the treatment of hernias via coelioscopy. Indeed, such prostheses may be wound around themselves, with the barbs on the inside and/or on the outside and be thus transported in the channel of a trocar to the implantation site without risk of damaging the barbs. Furthermore, due to the fact of the presence of the microporous layer on the second face of the fabric and of the coating made of water-soluble material of the barbs, the barbs do not obstruct the deployment of the prosthesis once it has been released from the trocar at the implantation site.

EXAMPLE 1D

Covering the Barbs of the Prosthetic Fabric of Example 1B with a Water Soluble Material:

Before packaging the prosthesis, the barbs of the prosthetic fabric of Example 1B are covered with a water soluble material in the same manner as described in Example 1C.

EXAMPLE 2

The same initial prosthetic fabric as in EXAMPLE 1A above and represented in FIG. 1 is provided.

1°) Preparation of the Solution of Bioresorbable Material in Order to Form the Microporous Layer:

A sterile concentrated solution of PEG 4000 (polyethylene glycol having a molar mass of 4000 daltons, for example sold by Fluka under the trade name PEG 4000) and of glycerol (also sold by Fluka) is added to a solution of gelatin (obtained by acid hydrolysis or by alkaline hydrolysis, for example sold by Sigma) at the concentration of 3% w/v, so as to obtain a mixture containing PEG 4000 at the final concentration of 1% w/v and glycerol at the final concentration of 0.6% w/v. The pH of the solution is adjusted to 7.0 by adding a concentrated solution of sodium hydroxide. The volume of the solution is then topped up with sterile water so as to obtain final concentrations of gelatin, of PEG 4000 and of glycerol of 2.7% w/v, of 0.9% w/v and of 0.54% w/v, respectively.

2°) Covering of Face 2b of the Prosthetic Fabric:

The solution obtained in 1°) is spread so as to form a thin layer with a density of 0.133 g/cm² on a flat hydrophobic inert support made of PVC or of polystyrene. The surface is then exposed to a flow of sterile air at ambient temperature for between 5 and 60 minutes, in order to allow the solution obtained in 1°) to gel. The second face 2b of the prosthetic fabric is then gently applied to the gelled layer of said solution. The whole assembly is exposed to a flow of sterile air, at ambient temperature, until complete evaporation is achieved, in around 18 hours.

A barbed prosthetic fabric is obtained which is covered on its face that does not comprise the barbs with a microporous layer in the form of a continuous film.

The relative concentrations of gelatin, of PEG and of glycerol are 3/1/0.6, w/w/w, in the non-porous layer, after drying.

The prosthetic fabric covered as described above is then detached from the inert support. As in the preceding example, the film forming the microporous layer is substantially free of pores and its outer surface is essentially smooth.

3°) Covering the Barbs with a Water Soluble Material:

The barbs are covered with a water soluble material using the same method as that described in Example 1C.

The covered prosthetic fabric thus obtained may be packed in a sterile double bag. It is then sterilized, preferably by γ irradiation, at a dose ranging from 25 to 45 kGy. It is then stored at ambient temperature until it is used, for example in order to manufacture a prosthesis.

EXAMPLE 3

The same initial prosthetic fabric as in EXAMPLE 1A above, described in FIG. 1, is provided.

1°) Preparation of the Solution of Bioresorbable Material in Order to Form the Microporous Layer:

A solution of polyvinyl alcohol (PVA) (provided by Sigma Aldrich, in 87-89% hydrolysed form, Mw=31,000-50,000) is prepared at 8% w/v in solution by heating at 90° C., using a magnetic hot plate stirrer, 4% glycerol is added, then the solution is cooled to 40° C.

2°) Covering of Face 2b of the Prosthetic Fabric:

30 ml of the solution obtained in 1°) is cast on a 12 cm×17 cm silicone frame. The second face 2b of the prosthetic fabric is placed on said solution. After drying for around 10 hours under a laminar flow hood, the layer of solution is at least partially gelled and the prosthetic fabric thus covered is detached from the frame. A prosthetic fabric according to the invention is obtained, covered on its face that does not comprise the barbs with a microporous layer in the form of a PVA film. This PVA film is not soluble at ambient temperature but becomes so at 37° C. The PVA film thus obtained has a smooth outer surface that is free of pores, in particular free of pores having a size strictly greater than 300 μm.

3°) Covering the Barbs with a Water Soluble Material:

The barbs are covered with a water soluble material using the same method as that described in Example 1C.

The prosthetic fabric thus covered is packaged in sealed bags and is sterilized by β or γ irradiation or by EtO. After sterilization using ethylene oxide or via beta or gamma irradiation, the covered prosthetic fabric is heated in an oven at 50° C. for around 50 hours.

The thus coated covered prosthetic fabric makes it possible to produce prostheses which can easily be wound around themselves in order to be introduced into a trocar: by virtue of the presence of the microporous layer on the face that does not comprise the barbs and of the water-soluble material on the barbs, the latter do not become entangled with one another during the rolling up of the prosthesis. The unrolling and the positioning of the prosthesis on exiting the trocar are thus facilitated.

EXAMPLE 4

The same initial prosthetic fabric as in EXAMPLE 1A above, described in FIG. 1, is provided.

1°) Preparation of Two Solutions of Bioresorbable Material in Order to Form the Microporous Layer:

a) a solution of oxidized collagen at 3.4% w/v and glycerol at 1.4% w/v is prepared as described in example 1.

b) a solution of polyvinyl alcohol (PVA) (provided by Sigma Aldrich, in 87-89% hydrolysed form, Mw=31,000-50,000) is prepared at 3.4% w/v in solution by heating at 90° C. using a magnetic hot plate stirrer, then the solution is cooled and is kept at 40° C.

c) 50% (w/w) of the PVA solution obtained in b) is mixed with 50% (w/w) of the oxidized collagen/glycerol solution obtained in a) in order to obtain a first film. After mixing the two compounds, the solution is neutralized at pH 7, using a 1M sodium hydroxide solution.

d) a solution is prepared composed of oxidized collagen, PVA and glycerol in the following proportions, given by weight: 2.7% of oxidized collagen, 0.35% of PVA and 0.35% of glycerol. Thus, this solution comprises the same components as the solution obtained in c), but in different proportions.

2°) Covering of Face 2b of the Prosthetic Fabric:

a) Obtaining a First Film:

30 ml of the solution obtained in 1° c.) are cast on a 12 cm×17 cm silicone frame. Gelling appears after 20 to 30 minutes at ambient temperature. A first film is obtained.

b) Obtaining a Second Film:

1 hour after the casting carried out in a), the solution obtained in 1° d) is cast over the first film. The gelling of this new layer appears after 20 to 30 minutes. Drying is carried out under a laminar flow hood at ambient temperature for around 10 to around 14 hours.

A prosthetic fabric according to the invention is obtained covered on its face that does not comprise the barbs with a microporous layer in the form of a two-layer film. The complete covering of the face that does not comprise the barbs is thus facilitated.

After sterilization using ethylene oxide, or via beta or gamma irradiation, the prosthetic fabric is heated in an oven at 50° C. for around 48 hours.

In wet form, the two-layer film obtained according to the present example does not exhibit delamination of the two superposed layers in an aqueous medium. Furthermore, this two-layer film exhibits good elasticity. The outer surface of this two-layer film is smooth and free of pores, in particular pores having a size strictly greater than 300 μm.

3°) Covering the Barbs with a Water Soluble Material:

The barbs are covered with a water soluble material using the same method as that described in Example 1C.

EXAMPLE 5

The same initial prosthetic fabric as in EXAMPLE 1A above and represented in FIG. 1 is provided.

Figure 3:
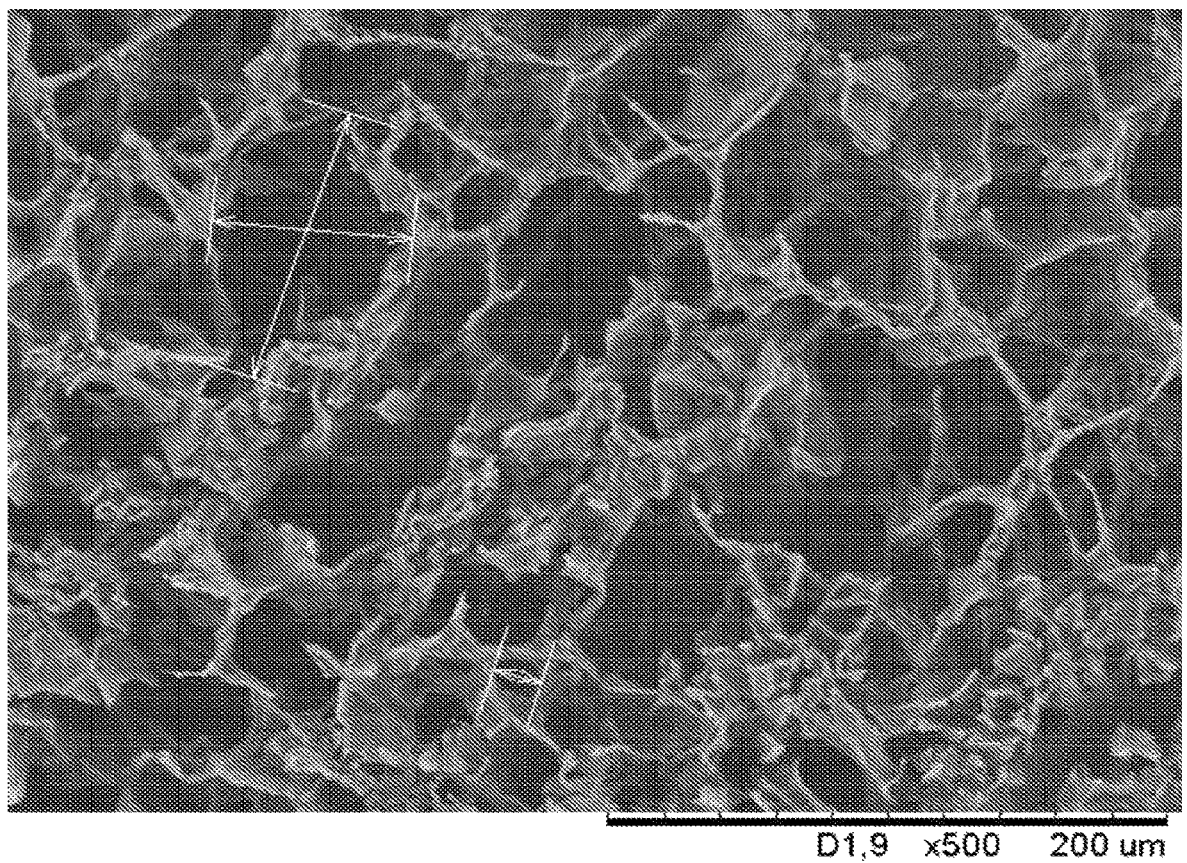
FIG. 3 is a photo taken with a scanning electron microscope of TM-1000 type, supplied by Hitachi, with a ×500 magnification, of the microporous layer of one embodiment of a prosthetic fabric according to the invention.

1°) Preparation of the Solution of Bioresorbable Material in Order to Form the Microporous Layer:

8 g of pork gelatin (supplier: Sigma Aldrich) are dissolved in 92 ml of a 5% w/v aqueous solution of glycerol. The gelatin solution is dissolved at 45° C. with magnetic stirring, then heated for 10 minutes at 50° C. 30 ml of the solution obtained is hot-cast in a 12 cm×17 cm box, and the face 2*b* of the prosthetic fabric is placed directly onto the solution. After gelling of the gelatin solution at ambient temperature, the boxes are freeze-dried for 20 hours. The prosthetic fabric covered with the layer of gelatin is easily removed from the box. The layer or membrane of gelatin has a microporous structure: the membrane, and for example its outer surface, has pores with a size that varies from 20 to 120 μm, but does not have pores with a size greater than 300 μm: a photo of this membrane taken with a scanning electron microscope is represented in FIG. 3: it clearly appears from this photo that the microporous layer or membrane is free of pores with a size greater than 300 μm. Thus, when the prosthetic fabric thus obtained is wound around itself, the barbs do not penetrate within the pores having a size ranging from 20 to 120 μm of the microporous layer. The barbs slide over the outer surface of the microporous layer and do not become entangled with one another.

The unrolling and the positioning of a prosthesis made from such a fabric, on exiting the trocar, are thus facilitated.

2°) Covering the Barbs with a Water Soluble Material:

The barbs are covered with a water soluble material using the same method as that described in Example 1C.

Barbed fabrics coated with a microporous layer as described in Examples 1 to 5 above are particularly suitable for the manufacture of prostheses for the treatment of hernias via coelioscopy. Indeed, such prostheses may be wound around themselves, with the barbs on the inside and/or on the outside and be thus conveyed in the channel of a trocar to the implantation site without risk of entanglement or damaging of the barbs. Furthermore, due to the presence of the microporous layer and optionally of the water-soluble material on the barbs, the barbs do not become entangled in the body of the fabric and do not obstruct the deployment of the prosthesis once it is released from the trocar at the implantation site: once the prosthesis is unwound and optionally after dissolving of the water-soluble material, the barbs, by virtue of their coupling properties, may be used to fasten the prosthesis in the manner desired by the surgeon.

EXAMPLE 6

Covered prosthetic fabrics such as that described in examples 1C, 1 D and 2-5 are manufactured wherein the water soluble material used for covering the barbs further includes a bioactive agent.

Such a covered prosthetic fabric as described in Example 1D for which the water soluble material further includes a bioactive agent may be used for releasing in the body of the patient one or more bioactive agents in a sequential manner.

The invention claimed is:

1. A process for covering a prosthetic fabric having an arrangement of yarns that define first and second faces for the fabric, the fabric including, over at least the first face, one or more barbs that protrude outwards relative to the first face, the process comprising
applying a layer of a first solution including at least one bioresorbable material to an inert support;
applying the second face of the fabric to the layer when the layer is at least partially gelled; and
applying a layer of a composition including at least one water-soluble biocompatible material to the one or more barbs over at least the first face.

2. The process according to claim 1, further comprising preparing the solution including at least one bioresorbable material prior to applying to an inert support.

3. The process according to claim 1, further comprising preparing the composition including at least one water-soluble biocompatible material prior to applying to the one or more barbs.

4. The process according to claim 1, wherein the step of applying the layer of the composition including at least one water-soluble biocompatible material to the one or more barbs is carried out prior to one or more of the steps of applying the layer of the first solution including at least one bioresorbable material to the inert support or applying the second face of the fabric to the layer when the layer is at least partially gelled.

5. The process according to claim 1, wherein the step of applying the layer of the composition including at least one water-soluble biocompatible material to the one or more barbs is carried out after to one or more of the steps of applying the layer of the first solution including at least one bioresorbable material to the inert support or applying the second face of the fabric to the layer when the layer is at least partially gelled.

6. The process according to claim 1, further comprising applying a layer of a second solution of at least one bioresorbable material to the partially gelled layer before the application of the second face of the fabric.

7. The process according to claim 6, wherein the second solution of at least one bioresorbable material is different from the first solution of at least one bioresorbable material.

8. The process according to claim 7, wherein the second solution includes the same at least one bioresorbable material of the first solution but in a different proportion.

9. The process according to claim 1, further comprising freeze drying the fabric for a duration ranging from 20 to 60 hours to form an impenetrable film on the second face, after the step of applying the second face of the fabric to the layer when the layer is at least partially gelled.

10. The process according to claim 9, wherein the impenetrable film has pores ranging from 20 to 120 μm.

11. The process according to claim 1, wherein applying a layer of the composition to the one or more barbs includes using a roll.

12. The process according to claim 1, wherein the layer of the composition is applied uniformly to the one or more barbs.

13. The process according to claim 1, wherein the at least one bioresorbable material is selected from the group consisting of collagen compounds, hydrophilic macromolecular compounds, polyvinyl alcohols, glycerols and mixtures thereof.

14. The process according to claim 13, wherein the at least one bioresorbable material includes at least one collagen compound.

15. The process according to claim 13, wherein the at least one bioresorbable material includes the hydrophilic macromolecular compounds selected from the group consisting of polyalkylene glycols, such as polyethylene glycol or polypropylene glycol, polysaccharides, such as starch, dextran and/or derivatives of cellulose, oxidized polysaccharides, mucopolysaccharides, and mixtures thereof.

16. The process according to claim 13, wherein the at least one bioresorbable material includes glycerol.

17. The process according to claim 13, wherein the at least one bioresorbable material includes polyvinyl alcohol.

18. The process according to claim 1, wherein the at least one water-soluble material is selected from the group consisting of polyethylene glycols, polyvinyl acetates, gelatin, polyglucuronic acid, hyaluronic acid, carboxymethyl cellulose, cellulose ethers, chitosan and mixtures thereof.

19. The process according to claim 1, wherein at least one of the first solution or the composition further comprises at least one bioactive agent.

\* \* \* \* \*